(12) United States Patent
Kramer et al.

(10) Patent No.: US 9,850,260 B2
(45) Date of Patent: *Dec. 26, 2017

(54) HYDROXYMETHYL-CARBOXAMIDO-SUBSTITUTED SILANE AND ITS USE FOR CURABLE, SILANE-TERMINATED POLYMERS

(71) Applicant: SIKA TECHNOLOGY AG, Baar (CH)

(72) Inventors: Andreas Kramer, Zürich (CH); Urs Burckhardt, Zürich (CH); Ursula Stadelmann, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/903,796

(22) PCT Filed: Jul. 24, 2014

(86) PCT No.: PCT/EP2014/065984
§ 371 (c)(1),
(2) Date: Jan. 8, 2016

(87) PCT Pub. No.: WO2015/014726
PCT Pub. Date: Feb. 5, 2015

(65) Prior Publication Data
US 2016/0159833 A1 Jun. 9, 2016

(30) Foreign Application Priority Data
Jul. 30, 2013 (EP) .................................. 13178563

(51) Int. Cl.
| | | |
|---|---|---|
| *C07F 7/10* | (2006.01) | |
| *C07F 7/18* | (2006.01) | |
| *C08G 18/48* | (2006.01) | |
| *C08G 18/75* | (2006.01) | |
| *C08G 18/76* | (2006.01) | |
| *C08G 18/80* | (2006.01) | |
| *C08G 18/10* | (2006.01) | |
| *C08G 18/28* | (2006.01) | |
| *C08G 18/83* | (2006.01) | |

(52) U.S. Cl.
CPC .......... *C07F 7/1804* (2013.01); *C07F 7/1836* (2013.01); *C07F 7/1892* (2013.01); *C08G 18/10* (2013.01); *C08G 18/289* (2013.01); *C08G 18/4825* (2013.01); *C08G 18/755* (2013.01); *C08G 18/7621* (2013.01); *C08G 18/7671* (2013.01); *C08G 18/809* (2013.01); *C08G 18/837* (2013.01)

(58) Field of Classification Search
CPC ........ C07F 7/081; C07F 7/182; C07F 7/1836; C08G 18/289; C08G 18/837
See application file for complete search history.

(56) References Cited

U.S. PATENT DOCUMENTS

| | | | | |
|---|---|---|---|---|
| 4,104,296 | A * | 8/1978 | Pike ........................ | C07F 7/182 528/26 |
| 5,587,502 | A | 12/1996 | Moren et al. | |
| 2009/0018302 | A1 | 1/2009 | Laas et al. | |
| 2010/0143712 | A1 | 6/2010 | Plantenberg et al. | |
| 2011/0034627 | A1* | 2/2011 | Boudet .................. | C08G 18/10 524/588 |
| 2011/0082273 | A1 | 4/2011 | Laas et al. | |

FOREIGN PATENT DOCUMENTS

| | | |
|---|---|---|
| CN | 101239987 A | 8/2008 |
| CN | 102030883 A | 4/2011 |
| DE | 10 2007 038 661 A1 | 2/2009 |
| DE | 10 2008 020 979 A1 | 10/2009 |
| EP | 2014692 A2 | 1/2009 |
| SU | 555104 A1 | 4/1977 |
| WO | 2013/174891 A2 | 11/2013 |

OTHER PUBLICATIONS

Feb. 2, 2016 International Preliminary Report on Patentability issued in International Patent Application No. PCT/EP2014/065984.
Dec. 16, 2014 Search Report issued in International Patent Application No. PCT/EP2014/065983.
Feb. 2, 2016 International Preliminary Report on Patentability issued in International Patent Application No. PCT/ EP2014/065983.
Dec. 5, 2016 Office Action Issued in U.S Appl. No. 14/901,492.
Niaoki et al., "Preparation of Oligosaccharide-Modified Silica Gel as Resolving Agent for Chromatography," Chemical Abstracts Service, 1994, XP-002718613.
Sep. 8, 2014 International Search Report issued in International Patent Application No. PCT/EP2014/065984.
Jun. 28, 1991 RN: 134579-64-9, STN Columbus Database Registry, 5 pgs.

* cited by examiner

*Primary Examiner* — Margaret Moore
(74) *Attorney, Agent, or Firm* — Oliff PLC

(57) ABSTRACT

Specific hydroxysilanes of formula (I), a method for the production thereof, the use thereof as a constituent of moisture-curing compositions, and silane-functional compounds produced therefrom, in particular silane-functional polymers and isocyanatosilanes. The hydrosilanes can be produced in a simple process with a high degree of purity and are storage-stable after production. Production from the reaction of lactides with aminosilanes is particularly advantageous. Hydroxysilane of formula (I), where n is 1 or 2.

15 Claims, No Drawings

HYDROXYMETHYL-CARBOXAMIDO-SUBSTITUTED SILANE AND ITS USE FOR CURABLE, SILANE-TERMINATED POLYMERS

TECHNICAL FIELD

The invention relates to hydroxysilanes and their use.

PRIOR ART

Organosilanes with an additional functional group are often used in sealants, adhesives, coatings and pretreatment agents such as primers or activators. They serve, inter alia, as adhesion promoters or crosslinkers, and also as structural components for the preparation of compounds containing silane groups. Of importance are in particular polymers containing silane groups, also referred to as "silane-functional polymers" or "silane-modified polymers" (SMP) or "silane-terminated polymers" (STP) which are crosslinkable by means of moisture and serve as binders in curable compositions.

Typical organosilanes which can be reacted with isocyanates in a simple manner to give silane-functional compounds are mercaptosilanes and amino-silanes. However, these have disadvantages. Mercaptosilanes have an unpleasant odor and, with isocyanates, form thiourethanes that are not very thermally stable and which can be readily back-cleaved at elevated temperature. Aminosilanes are basic and, with isocyanates, form ureas which often have a very high viscosity or limited thermal stability.

Hydroxysilanes are less known from the prior art. Their handling has the difficulty that, on account of a rapid reaction of the hydroxyl group with the silane group, they have a tendency towards self-condensation and are therefore often very impure and/or not very storage-stable. For the reaction with isocyanates, however, hydroxysilanes would be of interest since the urethanes that are produced in said reaction are relatively thermally stable and have a moderate viscosity.

U.S. Pat. No. 5,587,502 discloses hydroxycarbamoylsilanes. However, the described hydroxysilanes have too low a purity to be really interesting for the preparation of silane-functional polymers, and their hydroxyl group is not very reactive.

DESCRIPTION OF THE INVENTION

It is therefore an object of the present invention to provide a hydroxysilane which can be prepared in high purity in a simple process, has good storage stability and is suitable for producing silane-functional compounds.

Surprisingly, it has been found that a hydroxysilane as claimed in claim 1 achieves this object. The hydroxysilane as claimed in claim 1 can be prepared in high purity in a simple process from commercially readily available raw materials. It has a hydroxyl group of high reactivity and good storage stability. The hydroxysilane as claimed in claim 1 can advantageously be used as a constituent of a curable composition, in particular of an activator, of a primer, of an adhesive or sealant or of a coating, where it can act as adhesion promoter and/or crosslinker without having the disadvantages of mercapto- or aminosilanes such as unpleasant odors or strong basicity. It can be used particularly advantageously for the preparation of silane-functional compounds, especially by reacting it with isocyanates. Such silane-functional compounds can be used in the same way as the hydroxysilane itself. Additionally, they can be used as moisture-curing binder in curable compositions.

Silane-functional polymers from the reaction of a hydroxysilane of the formula (I) with isocyanate-functional polyurethane polymers have particularly advantageous properties. The polymers thus obtained rapidly cure with moisture to give elastic materials of high strength, elasticity and thermal stability and adhere well to a large number of substrates.

Further aspects of the invention are the subject of further independent claims. Particularly preferred embodiments of the invention are the subject of the dependent claims.

Ways of Carrying Out the Invention

The invention provides a hydroxysilane of the formula (I),

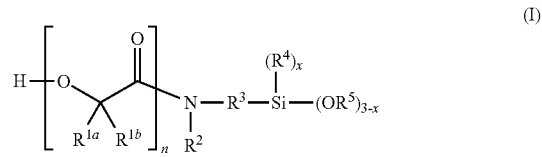

where
$R^{1a}$ and $R^{1b}$, independently of one another, are in each case a hydrogen atom or a monovalent hydrocarbon radical having 1 to 12 carbon atoms, or together are an alkylene radical having 2 to 6 carbon atoms;
$R^2$ is a hydrogen atom or a monovalent hydrocarbon radical having 1 to 12 carbon atoms which optionally comprises ether groups, ester groups, nitrile groups, amino groups or silane groups;
$R^3$ is a linear or branched alkylene or cycloalkylene radical having 1 to 20 carbon atoms, optionally with aromatic fractions, and optionally with one or more heteroatoms, in particular nitrogen atoms;
$R^4$ is an alkyl radical having 1 to 8 carbon atoms;
$R^5$ is an alkyl radical having 1 to 10 carbon atoms which optionally comprises ether groups;
n is 1 or 2; and
x is 0, 1 or 2.

In the present document, the term "alkoxysilane group" or for short "silane group" refers to a silyl group bonded to an organic radical and having one to three, in particular two or three, hydrolyzable alkoxy radicals on the silicon atom.

Accordingly, the term "alkoxysilane" or for short "silane" refers to an organic compound which has at least one silane group.

"Hydroxysilane", "isocyanatosilane", "aminosilane" and "mercaptosilane" are used to refer to silanes which have one or more hydroxyl, isocyanato, amino or mercapto groups on the organic radical in addition to the silane group.

Substance names starting with "poly", such as polyol or polyisocyanate, refer to substances which formally comprise two or more of the functional groups occurring in their name per molecule.

The term "polyurethane polymer" includes all polymers which are prepared by the so-called diisocyanate polyaddition process. The term "polyurethane polymer" also includes polyurethane polymers having isocyanate groups as are obtainable from the reaction of polyols with an excess of polyisocyanates and are themselves polyisocyanates and are often also called prepolymers.

In the present document, "molecular weight" is understood as meaning the molar mass (in grams per mole) of a molecule. "Average molecular weight" refers to the number average $M_n$ of an oligomeric or polymeric mixture of molecules, which is usually determined by means of gel permeation chromatography (GPC) against polystyrene as standard.

A dashed line in the formulae in this document is in each case the bond between a substituent and the associated molecule radical.

A substance or a composition is referred to as "storage-stable" if it can be stored at room temperature in a suitable pack for a prolonged time, typically for several weeks up to 3 months and more, without changing in its application or use properties as a result of the storage to an extent relevant for its use. "Room temperature" refers to a temperature of about 23° C.

Hydroxysilanes of the formula (I) in which $R^{1a}$ and $R^{1b}$ are different substituents are chiral compounds which can be present in isomerically pure form or as isomer mixtures.

Preferably, $R^{1a}$ and $R^{1b}$ are in each case not a tertiary alkyl radical such as, for example, tert-butyl. A tertiary alkyl radical brings about considerable steric hindrance of the hydroxyl group, which may be disadvantageous for the use of the hydroxysilane.

$R^{1a}$ is preferably a hydrogen atom or a monovalent hydrocarbon radical having 1 to 6 carbon atoms which is not bonded via a tertiary carbon atom, in particular hydrogen, methyl, ethyl, n-propyl, isopropyl, butyl, sec-butyl, cyclopentyl, cyclohexyl or phenyl. Such a hydroxysilane has a hydroxyl group with good reactivity.

$R^{1a}$ is particularly preferably a hydrogen atom or a monovalent hydrocarbon radical having 1 to 6 carbon atoms which is bonded via a primary carbon atom, in particular hydrogen, methyl, ethyl, n-propyl, butyl or sec-butyl. Such a hydroxysilane has a hydroxyl group with very good reactivity.

$R^{1a}$ is in particular a hydrogen atom or a methyl radical, most preferably a methyl radical.

A substituent $R^{1a}$ in the form of methyl is advantageous due to the fact that such hydroxysilanes are easily accessible and have good storage stability and the hydroxyl group is of high reactivity.

A substituent $R^{1a}$ in the form of hydrogen is advantageous due to the fact that the hydroxyl group is particularly reactive, which may be advantageous if the hydroxysilane is not to be stored too long.

$R^{1b}$ particularly preferably a hydrogen atom or a methyl radical, in particular a hydrogen atom.

Particularly preferably, $R^{1a}$ and $R^{1b}$, independently of one another, are in each case a hydrogen atom or a methyl radical. Such a hydroxysilane has a particularly reactive hydroxyl group and is very storage-stable.

Most preferably, $R^{1a}$ is a methyl radical and $R^{1b}$ is a hydrogen atom. Such a hydroxysilane is particularly easily accessible and has exceptional storage stability, and the hydroxyl group is of very high reactivity.

$R^2$ is preferably a hydrogen atom or an alkyl radical or a cycloalkyl radical or an alkoxysilylalkyl radical. Such a hydroxysilane is particularly easily accessible.

$R^2$ is particularly preferably a hydrogen atom. Such a hydroxysilane can be prepared particularly readily.

$R^2$ is furthermore particularly preferably an alkoxysilylalkyl radical, in particular trimethoxysilylpropyl or triethoxysilylpropyl. Such a hydroxysilane of the formula (I) permits particularly good adhesion properties.

$R^3$ is preferably a linear or branched alkylene radical having 1 to 6 carbon atoms, optionally with a nitrogen atom.

Particularly preferably, the radical $R^3$ is selected from the group consisting of 1,3-propylene, 4-aza-1,6-hexylene, 2-methyl-1,3-propylene, 1,4-butylene, 3-methyl-1,4-butylene and 3,3-dimethyl-1,4-butylene. Of these, particular preference is given to 1,3-propylene and 3,3-dimethyl-1,4-butylene, in particular 1,3-propylene.

The position of the substituents or heteroatoms in the radicals $R^3$ is numbered starting from the silicon atom.

Such a hydroxysilane of the formula (I) is particularly readily accessible.

$R^4$ is preferably a methyl radical.

$R^5$ is preferably a methyl radical or ethyl radical, most preferably an ethyl radical.

A hydroxysilane of the formula (I) with methoxy groups has the advantage that its silane groups are particularly reactive.

A hydroxysilane of the formula (I) with ethoxy groups has the advantage that it is particularly storage-stable and that during its hydrolysis the less toxic ethanol is released.

n is preferably 1. Such a hydroxysilane is free from ester groups. It cannot transesterify with alcohol released during the silane hydrolysis, as a result of which it is particularly storage-stable.

x is preferably 0 or 1, in particular 0. Such a hydroxysilane has particularly reactive silane groups.

The hydroxysilane of the formula (I) is preferably selected from the group consisting of N-(3-triethoxysilylpropyl)-2-hydroxyacetamide, N-(3-trimethoxysilylpropyl)-2-hydroxyacetamide, N-(3-diethoxymethylsilylpropyl)-2-hydroxyacetamide, N-(3-dimethoxymethylsilylpropyl)-2-hydroxyacetamide, N-(3-triethoxysilylpropyl)-2-hydroxypropanamide, N-(3-trimethoxysilylpropyl)-2-hydroxypropanamide, N-(3-diethoxymethylsilylpropyl)-2-hydroxypropanamide, N-(3-dimethoxymethylsilylpropyl)-2-hydroxypropanamide, N-(3-triethoxysilylpropyl)-2-hydroxy-2-methylpropanamide, N-(3-trimethoxysilylpropyl)-2-hydroxy-2-methylpropanamide, N-(3-diethoxymethylsilylpropyl)-2-hydroxy-2-methylpropanamide and N-(3-dimethoxymethylsilylpropyl)-2-hydroxy-2-methylpropanamide.

These hydroxysilanes are readily accessible and their hydroxyl group is of very good reactivity.

Of these, preference is given to the trialkoxysilanes, in particular the triethoxysilanes.

Particular preference is given to N-(3-trimethoxysilylpropyl)-2-hydroxypropanamide N-(3-triethoxysilylpropyl)-2-hydroxypropanamide. N-(3-Triethoxysilylpropyl)-2-hydroxypropanamide is most preferred. It is particularly storage-stable and ethanol is released during its hydrolysis, which may be advantageous for toxicological reasons.

The invention further provides a process for the preparation of a hydroxysilane of the formula (I) by reaction of
at least one lactide of the formula (II) or at least one hydroxy ester of the formula (III) with
at least one aminosilane of the formula (IV).

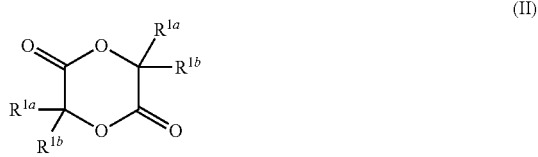

(II)

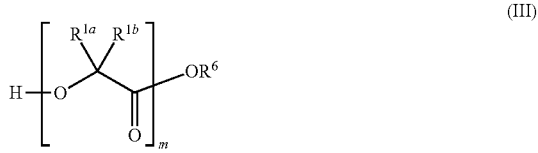

(III)

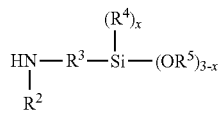

(IV)

In the formulae (II), (III) and (IV), m is an integer from 1 to 100;

$R^6$ is a monovalent hydrocarbon radical having 1 to 12 carbon atoms; and $R^{1a}$, $R^{1b}$, $R^2$, $R^3$, $R^4$, $R^5$ and x have the meanings already specified.

In the case of a lactide of the formula (II), this reaction is preferably carried out under the exclusion of moisture at a temperature in the range from 15 to 120° C., in particular 20 to 90° C., optionally in the presence of a catalyst and/or a drying agent such as, in particular, vinyltriethoxysilane, tetraethoxysilane, vinyltrimethoxysilane or a molecular sieve. Preferably approximately two moles of aminosilane are used per mole of lactide. In this way, primarily hydroxysilanes of the formula (I) where n=1 are formed. However, it is also possible for approximately one mole of aminosilane to be used per mole of lactide, in which case primarily hydroxysilanes of the formula (I) where n=2 are formed. Preference is given to working with an aminosilane/lactide ratio in the range from 1.8 to 2.2. The reaction can take place without a solvent or in a suitable solvent. Volatile compounds possibly present after the reaction, in particular solvents, unreacted starting materials or released alcohol, can be removed from the reaction product by distillation.

In the case of a hydroxy ester of the formula (III), this reaction is preferably performed with moisture exclusion at a temperature in the range from 40 to 150° C., optionally in the presence of a drying agent such as, in particular, vinyltriethoxysilane, tetraethoxysilane, vinyltrimethoxysilane or a molecular sieve. During this reaction, preference is given to using a catalyst, in particular a metal compound, in particular a titanate, a stannate or an aluminate. Preferably approximately one mole of aminosilane of the formula (IV) is used per ester group of the hydroxy ester of the formula (III). A hydroxy ester of the formula (III) in which m is 1 is thus preferably reacted with the aminosilane approximately in the molar ratio 1:1. A polymeric hydroxy ester in which, for example, m is 10 is accordingly preferably reacted with the aminosilane approximately in the molar ratio 1:10. In this way, primarily hydroxysilanes of the formula (I) are formed in which n is 1. Preference is given to working with an aminosilane/hydroxy ester ratio in the range from (0.8 to 1.2)m. The reaction can take place without a solvent or in a suitable solvent. Preferably, after the reaction, the released alcohol, together with further volatile compounds possibly present, in particular solvents or unreacted starting materials, is removed from the reaction product by distillation.

Suitable lactides of the formula (II) are in particular 1,4-dioxane-2,5-dione (lactide of 2-hydroxyacetic acid, also called "glycolide"), 3,6-dimethyl-1,4-dioxane-2,5-dione (lactide from lactic acid, also called "lactide") and 3,6-diphenyl-1,4-dioxane-2,5-dione (lactide from mandelic acid). These lactides are particularly readily accessible.

Preference is given to 1,4-dioxane-2,5-dione and 3,6-dimethyl-1,4-dioxane-2,5-dione. Hydroxysilanes with good storage stability and a very reactive hydroxyl group are obtainable from these lactides.

Particular preference is given to 3,6-dimethyl-1,4-dioxane-2,5-dione. Hydroxy-silanes with a particularly good storage stability and a very reactive hydroxyl group are obtainable from this lactide. In particular, the lactide from L-lactic acid, also called L-lactide or (3S,6S)-3,6-dimethyl-1,4-dioxane-2,5-dione, is particularly readily accessible, and here it is a renewable raw material.

Suitable hydroxy esters of the formula (III) are in particular the methyl esters, ethyl esters, isopropyl esters, n-propyl esters, tert-butyl esters, n-butyl esters and sec-butyl esters of 2-hydroxyacetic acid, 2-hydroxypropionic acid (lactic acid), 2-hydroxybutyric acid, 2-hydroxy-2-methylpropionic acid (2-hydroxyisobutyric acid), 2-hydroxypentanoic acid, 2-hydroxy-3-methylbutyric acid, 2-hydroxyhexanoic acid, 2-hydroxy-4-methylpentanoic acid, 2-hydroxy-2-cyclohexylacetic acid (hexahydromandelic acid), 2-hydroxy-2-phenylacetic acid (mandelic acid), 2-hydroxy-2-cyclopentylacetic acid and 2-hydroxy-2-cyclohexylacetic acid, as well as oligomeric forms of these hydroxy esters, i.e. compounds of the formula (III) where m>1.

Preference is given to the methyl esters and the ethyl esters of 2-hydroxyacetic acid, lactic acid, 2-hydroxyisobutyric acid and oligomeric forms of these hydroxy esters. Here, the methyl esters are preferred for the reaction with aminosilanes with methoxy groups and the ethyl esters are preferred for the reaction with aminosilanes with ethoxy groups.

Particular preference is given to lactic acid methyl esters and lactic acid ethyl esters and oligomeric forms thereof, in particular L-lactic acid methyl esters and L-lactic acid ethyl esters. The L-lactic acid esters are renewable raw materials. L-lactic acid ethyl ester is most preferred.

Suitable aminosilanes of the formula (IV) are, in particular, aminosilanes with a primary amino group, in particular 3-aminopropyltriethoxysilane, 3-aminopropyltrimethoxysilane, 3-aminopropyldiethoxymethylsilane, 3-aminopropyldimethoxymethylsilane, N-aminoethyl-3-aminopropyltriethoxysilane, N-aminoethyl-3-aminopropyltrimethoxysilane, N-aminoethyl-3-aminopropyldiethoxymethylsilane, N-aminoethyl-3-aminopropyldimethoxymethylsilane, 4-aminobutyltriethoxysilane, 4-aminobutyltrimethoxysilane, 4-aminobutyldiethoxy-methylsilane, 4-aminobutyldimethoxymethylsilane, 4-amino-3-methylbutyltri-ethoxysilane, 4-amino-3-methylbutyltrimethoxysilane, 4-amino-3-methylbutyl-diethoxymethylsilane, 4-amino-3-methylbutyldimethoxymethylsilane, 4-amino-3,3-dimethylbutyltriethoxysilane, 4-amino-3,3-dimethylbutyltrimethoxysilane, 4-amino-3,3-dimethylbutyldiethoxymethylsilane, 4-amino-3,3-dimethylbutyldimethoxymethylsilane, aminomethyltriethoxysilane, aminomethyltrimethoxy-silane, aminomethyldiethoxymethylsilane and aminomethyldimethoxy-methylsilane.

Of these, preference is given to 3-aminopropyltriethoxysilane, 3-aminopropyltrimethoxysilane, 3-aminopropyldiethoxymethylsilane, 3-aminopropyldimethoxymethylsilane, 4-amino-3,3-dimethylbutyltriethoxysilane, 4-amino-3,3-dimethylbutyltrimethoxysilane, 4-amino-3,3-dimethylbutyldiethoxymethylsilane and 4-amino-3,3-dimethylbutyldimethoxymethylsilane.

Particular preference is given to 3-aminopropyltriethoxysilane and 3-aminopropyltrimethoxysilane, in particular 3-aminopropyltriethoxysilane.

Also suitable as aminosilanes of the formula (IV) are aminosilanes with a secondary amino group, in particular bis(trimethoxysilylpropyl)amine, bis(triethoxysilylpropyl)amine, N-methyl-3-aminopropyltrimethoxysilane, N-methyl-3-aminopropyltriethoxysilane, N-(n-butyl)-3- aminopropyltrimethoxysilane, N-(n-butyl)-3-aminopropyltriethoxysilane, N-ethyl-3-amino-2-methyl-propyltrimethoxysilane, N-ethyl-3-amino-2-methylpropyltriethoxysilane, N-(3-trimethoxysilylpropyl)aminosuccinic acid diethyl ester, N-(3-triethoxysilylpropyl)-aminosuccinic acid diethyl ester, N-cyclohexylaminomethyltriethoxysilane and N-cyclohexylaminomethyltrimethoxysilane.

Preferably, the process for the preparation of a hydroxysilane of the formula (I) is carried out with at least one lactide of the formula (II). This reaction can be carried out in a particularly simple manner under especially mild conditions. It is even possible to carry out the reaction without catalysts at room temperature and without distillative aftertreatment.

Very particular preference is given to a process for the preparation of a hydroxysilane of the formula (I) by the reaction of 3,6-dimethyl-1,4-dioxane-2,5-dione, in particular (3S,6S)-3,6-dimethyl-1,4-dioxane-2,5-dione, with an aminosilane of the formula (IV). A hydroxysilane of the formula (I) with very good storage stability and very reactive hydroxyl group is accessible by this process in a particularly simple manner under mild preparation conditions.

The hydroxysilane of the formula (I) can comprise consecutive products from the hydrolysis and/or condensation of the silane groups, including those from an intra- or intermolecular self-condensation with the hydroxyl group. For certain applications, such consecutive products may be advantageous, for example for adhesion promoter solutions or aqueous pretreatment agents.

The invention further provides a silane-functional compound obtained from the reaction of at least one of the hydroxysilanes of the formula (I) described above with at least one compound which comprises at least one group that is reactive towards hydroxyl groups.

The reaction is carried out in particular under the exclusion of moisture and under the conditions suitable for the particular reactive group.

The group that is reactive towards hydroxyl groups is preferably selected from the group consisting of isocyanate groups, epoxy groups, acrylate groups, methacrylate groups, anhydride groups, carboxylic acid groups, ester groups, carbonate groups and cyclocarbonate groups.

Of these, preference is given to isocyanate groups, anhydride groups, ester groups, carbonate groups and cyclocarbonate groups. These reactive groups can be reacted with the hydroxysilane of the formula (I) in a particularly simple manner.

Isocyanate groups are most preferred. Silane-functional compounds from the reaction of a hydroxysilane of the formula (I) with an isocyanate can be used particularly advantageously, in particular as drying agent and/or adhesion promoter and/or moisture-cure binder.

Silane-functional compounds from the reaction of a hydroxysilane of the formula (I) with an isocyanate have at least one silane group of the formula (V).

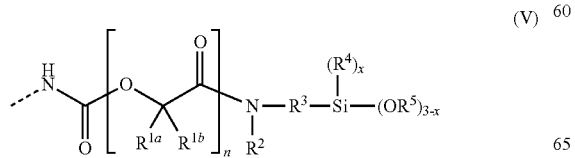

In the formula (V), $R^{1a}$, $R^{1b}$, $R^2$, $R^3$, $R^4$, $R^5$, n and x have the meanings already specified.

The reaction of the hydroxysilane of the formula (I) with the isocyanate is preferably carried out at a temperature in the range from 20 to 160° C. A catalyst is optionally used, in particular a tertiary amine or a metal compound, in particular a bismuth(III), zinc(II), zirconium(IV) or tin(II) compound or an organotin(IV) compound. Depending on the intended use of the silane-functional compound, the hydroxysilane of the formula (I) is used in a superstoichiometric, stoichiometric or substoichiometric ratio relative to the isocyanate groups.

For the use of the silane-functional compound as adhesion promoter, the hydroxysilane is preferably used in a substoichiometric amount. In particular, an OH/NCO ratio in the range from 0.1 to 0.5 is used here.

For the use of the silane-functional compound as moisture-cure binder, the hydroxysilane is preferably used in a stoichiometric amount or a slight superstoichiometric amount. In particular, an OH/NCO ratio in the range from 1 to 1.25 is used here.

Isocyanates suitable for the reaction with a hydroxysilane of the formula (I) are isocyanatosilanes, in particular 3-isocyanatopropyltrimethoxysilane, 3-isocyanatopropyltriethoxysilane, isocyanatomethyltrimethoxysilane and isocyanatomethyltriethoxysilane;

aliphatic and cycloaliphatic and aromatic monoisocyanates, in particular butyl isocyanate, hexyl isocyanate, lauryl isocyanate, stearyl isocyanate, cyclohexyl isocyanate and phenyl isocyanate;

aliphatic, arylaliphatic and cycloaliphatic di- and triisocyanates, in particular 1,4-tetramethylene diisocyanate, 2-methylpentamethylene 1,5-diisocyanate, 1,6-hexamethylene diisocyanate (HDI), 2,2,4- and 2,4,4-trimethyl-1,6-hexamethylene diisocyanate (TMDI), 1,10-decamethylene diisocyanate, 1,12-dodecamethylene diisocyanate, lysine and lysine ester diisocyanate, cyclohexane-1,3- and -1,4-diisocyanate, 1-methyl-2,4- and -2,6-diiso-cyanatocyclohexane and any desired mixtures of these isomers (HTDI or $H_6TDI$), 1-isocyanato-3,3,5-trimethyl-5-isocyanatomethylcyclohexane (=isophorone diisocyanate or IPDI), perhydro-2,4'- and -4,4'-diphenylmethane diisocyanate (HMDI or $H_{12}MDI$), 1,3- and 1,4-bis(isocyanato-methyl)cyclohexane, m- and p-xylylene diisocyanate (m- and p-XDI), tetramethyl-1,3- and -1,4-xylylene diisocyanate (m- and p-TMXDI), bis(1-isocyanato-1-methylethyl)naphthalene, dimer and trimer fatty acid isocyanates such as 3,6-bis(9-isocyanatononyl)-4,5-di(1-heptenyl)cyclo-hexene (dimeryl diisocyanate), preferably HDI and IPDI;

aromatic di- and triisocyanates, in particular 2,4- and/or 2,6-tolylene diisocyanate and any desired mixtures of these isomers (TDI), 4,4'-, 2,4'- and/or 2,2'-diphenylmethane diisocyanate and any desired mixtures of these isomers (MDI), mixtures of MDI and MDI homologs (polymeric MDI or PMDI), 1,3- and 1,4-phenylene diisocyanate, 2,3,5,6-tetramethyl-1,4-diisocyanatobenzene, naphthalene 1,5-diisocyanate (NDI), 3,3'-dimethyl-4,4'-diisocyanatodiphenyl (TODI), dianisidine diisocyanate (DADI), 1,3,5-tris(isocyanatomethyl)benzene, tris(4-isocyanatophenyl)methane and tris(4-isocyanatophenyl)thiophosphate, preferably MDI and TDI;

oligomers and derivatives of said di- and triisocyanates, in particular derived from HDI, IPDI, MDI and TDI; in particular commercially available grades, in particular HDI-biurets such as Desmodur® N 100 and N 3200 (from Bayer), Tolonate® HDB and HDB-LV (from Rhodia) and Duranate® 24A-100 (from Asahi Kasei); HDI isocyanurates, such as Desmodur® N 3300, N 3600 and N 3790 BA (all from Bayer), Tolonate® HDT, HDT-LV and HDT-LV2 (from Rhodia), Duranate® TPA-100 and THA-100 (from Asahi Kasei) and Coronate® HX (from Nippon Polyurethane); HDI uretdiones such as Desmodur® N 3400, Desmodur® XP 2840 (from Bayer); HDI iminooxa-diazinediones such as Desmodur® XP 2410 (from Bayer); HDI allophanatessuch as Desmodur® VP LS 2102, Desmodur® XP 2580 (from Bayer); IPDI isocyanurates, such as in particular in solution as Desmodur® Z 4470 (from Bayer) or in solid form as Vestanat® T1890/100 (from Evonik); TDI oligomers such as Desmodur® IL (from Bayer); and mixed isocyanurates based on TDI/HDI, for example as Desmodur® HL (from Bayer); furthermore forms of MDI liquid at room temperature (so-called "modified MDI"), which are mixtures of MDI with MDI derivatives, such as in particular MDI carbodiimides or MDI uretoneimines or MDI urethanes, known under trade names such as Desmodur® CD, Desmodur® PF, Desmodur® PC (all from Bayer) or Isonate® M 143 (from Dow), and mixtures of MDI and MDI homologs (polymeric MDI or PMDI), obtainable under trade names such as Desmodur® VL, Desmodur® VL50, Desmodur® VL R10, Desmodur® VL R20, Desmodur® VH 20 N and Desmodur® VKS 20F (all from Bayer), Isonate® M 309, Voranate® M 229 and Voranate® M 580 (all from Dow) or Lupranat® M 10 R (from BASF);

the specified oligomeric polyisocyanates are in practice usually mixtures of substances with different degrees of oligomerization and/or chemical structures; they preferably have an average NCO functionality of 2.1 to 4.0;

furthermore polymers having isocyanate groups, preferably obtainable from the reaction of at least one polyol with at least one polyisocyanate, the polyol used preferably being polyetherpolyols, polyesterpolyols, polycarbonatepolyols and polyacrylatepolyols, particularly preferably polyetherpolyols, in particular polyoxypropylenepolyols and polyoxyethylene-polyoxypropylene mixed polyols, and also polyester- and polycarbonatepolyols, in particular crystalline or amorphous polyesterpolyols that are solid at room temperature, with an average molecular weight in the range from 500 to 30 000 g/mol, preferably 1000 to 20 000 g/mol, in particular 2000 to 15 000 g/mol, and where the polyisocyanate used is preferably the specified diisocyanates, preferably MDI, TDI, HDI and IPDI, in particular IPDI.

Preferred isocyanates for the reaction with a hydroxysilane of the formula (I) are selected from the group consisting of isocyanatosilanes, diisocyanates, oligomers and derivatives thereof, and polymers having isocyanate groups. Particularly preferred isocyanates are selected from the group consisting of HDI, IPDI, MDI and TDI, and oligomers and derivatives of these isocyanates, and polymers having isocyanate groups derived from these isocyanates.

A particularly preferred silane-functional compound with at least one silane group of the formula (V) is a silane-functional polymer which can advantageously be used as binder for moisture-cure compositions. It is obtained in particular from the reaction of a hydroxysilane of the formula (I) with a polymer having isocyanate groups.

Such a silane-functional polymer preferably has 1 to 4, particularly preferably 1 to 3, in particular 2 or 3, terminal silane groups of the formula (V). It is preferably free from isocyanate groups.

Such a silane-functional polymer preferably has an average molecular weight in the range from 1000 to 30 000 g/mol, particularly preferably 2000 to 25 000 g/mol, in particular 3000 to 20 000 g/mol, most preferably 4000 to 15 000 g/mol.

A preferred silane-functional polymer has predominantly polyoxyalkylene units, in particular polyoxypropylene units. Its silane groups of the formula (V) are predominantly bonded to cycloaliphatic or aromatic radicals, in particular to cycloaliphatic radicals derived from IPDI. Such a polymer is suitable particularly as constituent of elastic coatings and elastic adhesives and/or sealants that can be applied at room temperature.

A further preferred silane-functional polymer has predominantly polyester and/or polycarbonate units, in particular polyester units, and is solid at room temperature. Its silane groups of the formula (V) are bonded predominantly to cycloaliphatic or aromatic radicals, in particular to aromatic radicals derived from MDI. Such a polymer is suitable in particular as constituent of adhesives that can be applied while hot, so-called hot-melt adhesives.

A further particularly preferred silane-functional compound with at least one silane group of the formula (V) is an isocyanatosilane of the formula (VI).

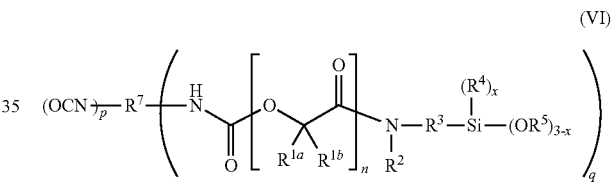

In the formula (VI), $R^7$ is a (p+q)-valent hydrocarbon radical having 4 to 50 carbon atoms, which optionally comprises carbodiimide, uretdione, allophanate, uretoneimine, biuret, iminooxadiazinedione, isocyanurate or urethane groups;

p is an integer from 1 to 4;

q is 1 or 2;

and $R^{1a}$, $R^{1b}$, $R^2$, $R^3$, $R^4$, $R^5$, n and x have the meanings already mentioned.

An isocyanatosilane of the formula (VI) is in particular obtained from the reaction of a hydroxysilane of the formula (I) with an aliphatic, arylaliphatic, cycloaliphatic or aromatic di- and triisocyanate or an oligomer or derivatives thereof.

Preferably, (p+q) is 2 or 3.

Particularly preferably, p and q are in each case 1 and $R^7$ is 1,6-hexylene, 2,2,4- and/or 2,4,4-trimethyl-1,6-hexylene, 1,3- and/or 1,4-cyclohexylene, 1,3- and/or 1,4-xylylene, 1,3- and/or 1,4-tetramethylxylylene, 4,4'- and/or 2,4'-substituted diphenylmethane, 2,4- and/or 2,6-substituted toluene, IPDI following removal of the two isocyanate groups or the uretdione of HDI following removal of the two isocyanate groups. Of these, preference is given to IPDI following removal of the two isocyanate groups.

Furthermore particularly preferably, (p+q) is 3 and $R^7$ is HDI biuret, HDI isocyanurate, IPDI isocyanurate, HDI iminooxadiazinedione, HDI allophanate or MDI uretoneimine in each case following removal of the three isocyanate groups.

These isocyanatosilanes are readily accessible, storage-stable substances. Particularly preferred isocyanatosilanes of the formula (VI) are selected from the group consisting of 1-oxo-1-((3-(triethoxysilyl)propyl)amino)-2-propyl ((5-isocyanato-1,3,3-trimethylcyclohexyl)methyl)carbamate; 1-oxo-1-((3-(triethoxysilyl)propyl)amino)-2-propyl 3,5,5-trimethyl-3-(isocyanatomethyl)cyclo-hexylcarbamate; 1-oxo-1-((3-(triethoxysilyl)propyl)amino)-2-propyl 4-methyl-3-isocyanatophenylcarbamate; 1-oxo-1-((3-(triethoxysilyl)propyl)amino)-2-propyl 2-methyl-3-isocyanatophenylcarbamate; and the corresponding compounds with trimethoxysilyl or with dimethoxymethylsilyl groups. Of these, particular preference is given to the cycloaliphatic compounds. They have particularly good storage stabilities.

An isocyanatosilane of the formula (VI) is particularly suitable as adhesion promoter, in particular as constituent of an adhesion promoter solution or of a primer, and as intermediate for the preparation of silane-functional polymers with at least one silane group of the formula (V). Of suitability for this are in particular isocyanatosilanes in which p and q are in each case 1. They can be reacted in particular with standard commercial polyols to give silane-functional polymers.

The invention further provides the use of a hydroxysilane of the formula (I) or of a silane-functional compound prepared therefrom as constituent of a curable composition. The hydroxysilane or the silane-functional compound prepared therefrom can act here in particular as drying agent and/or adhesion promoter and/or as moisture-cure binder.

The curable composition here is in particular a polyurethane composition having isocyanate groups, an epoxide resin composition or a composition having silane groups.

Such curable compositions can be used in particular as pretreatment agents, in particular as activator or primer, as pouring compound, sealant, adhesive, lining, coating or paint in the construction and production industry, in particular as joint sealant, parquet adhesive, assembly adhesive or hot-melt adhesive.

Preferably, the curable composition is a pretreatment agent or a coating or a sealant or an adhesive.

The adhesive is in particular an elastic or a (semi) structural adhesive or a hot-melt adhesive.

A pretreatment agent, in particular a primer or activator, comprises typically at least one solvent and optionally further constituents such as, in particular, catalysts, further silanes, titanates and zirconates and optionally fillers, wetting agents, polyisocyanates, polyurethane polymers having isocyanate and/or silane groups or epoxide resins.

A sealant or an elastic or (semi)structural adhesive typically comprises at least one moisture-cure binder, in particular a polymer having isocyanate groups or a silane-functional polymer, and optionally further constituents such as, in particular, catalysts, fillers, plasticizers and auxiliaries, in particular thickeners. A hot-melt adhesive typically comprises a moisture-crosslinking polymer that is solid at room temperature and optionally further constituents such as thermoplastic resins and polymers, fillers and auxiliaries.

The curable composition can advantageously be used for the coating or adhesion and/or sealing of substrates such as, in particular,
- glass, glass ceramic, concrete, mortar, brick, tiles, gypsum and natural stones such as granite or marble;
- metals and alloys, such as aluminum, iron, steel and nonferrous metals, and surface-refined metals and alloys, such as galvanized or chrome-plated metals;
- leather, textiles, paper, wood, wood materials bonded with resins, for example phenol, melamine or epoxide resins, resin/textile composite materials and other so-called polymer composites;
- plastics, such as polyvinyl chloride (rigid and flexible PVC), acrylonitrile-butadiene-styrene copolymers (ABS), polycarbonate (PC), polyamide (PA), polyesters, poly(methyl methacrylate) (PMMA), epoxide resins, polyurethanes (PUR), polyoxymethylene (POM), polyolefins (PO), polyethylene (PE) or polypropylene (PP), ethylene-propylene copolymers (EPM) and ethylene-propylene-diene terpolymers (EPDM), where the plastics may preferably be surface-treated by means of plasma, corona or flames;
- fiber-reinforced plastics, such as carbon-fiber-reinforced plastics (CFK), glass-fiber-reinforced plastics (GFK) and sheet molding compounds (SMC);
- coated substrates, such as powder-coated metals or alloys;
- paints and varnishes, in particular automobile finishing lacquers.

The substrates can be pretreated as required, for example by means of a physical and/or chemical cleaning or by means of applying an adhesion promoter, an adhesion promoter solution or a primer.

The stated uses of the hydroxysilane of the formula (I) or a silane-functional compound prepared therefrom gives rise to an article. This article is in particular a building of structural or civil engineering or an industrial product or a consumer product.

EXAMPLES

Working examples are listed hereinbelow which are intended to illustrate the described invention in more detail. The invention is of course not limited to these described working examples.

"Standard operating environment" is the term used to refer to a temperature of 23±1° C. and a relative atmospheric humidity of 50±5%. "NK" stands for "standard operating environment".

$^1$H NMR spectra were measured in $CDCl_3$ on a spectrometer of the type Bruker Ascend 400 at 400.14 MHz; the chemical shifts δ are given in ppm relative to tetramethylsilane (TMS), the coupling constants J are given in Hz. Infrared spectra (FT-IR) were measured as undiluted films on a Nicolet iS5 FT-IR instrument equipped with horizontal ATR measurement unit with diamond crystal from Thermo Scientific; the absorption bands are stated in wave numbers ($cm^{-1}$) (measurement window: 4000-650 $cm^{-1}$). The addition "sh" indicates a band appearing as a shoulder.

Gas chromatograms (GC) were measured in the temperature range from 60 to 320° C. with a heating rate of 30° C./min and a residence time of 15 min at 320° C. The injector temperature was 200° C. The detection was carried out by means of flame ionization (FID), the signals being evaluated via an area percent method.

Viscosities were measured on a thermostated Rheotec RC30 cone-plate viscometer (cone diameter 50 mm, cone angle 1°, cone point-plate distance 0.05 mm, shear rate 10 $s^{-1}$).

1. Preparation of Hydroxysilanes

Example 1a:
N-(3-Triethoxysilylpropyl)-2-hydroxypropanamide

In a round-bottomed flask, 36.00 g (162.6 mmol) of 3-aminopropyltriethoxysilane, 12.07 g (83.7 mmol) of L-lactide and 0.15 g of vinyltriethoxysilane were stirred under a nitrogen atmosphere for 3 h at 80° C. until reaction progress was no longer established by means of IR spectroscopy. The crude product was after-treated for 15 minutes at 60° C. and approx. 10 mbar. This gave a liquid product with a theoretical OH equivalent weight of 293.4 g/Eq, which was stored with moisture exclusion at room temperature.

FT-IR: 3406 sh (O—H), 3322 (N—H amide), 2974, 2928, 2885, 2736, 1741 (C=O ester), 1651 (C=O amide), 1535 (C=O amide), 1482, 1444, 1411, 1390, 1365, 1279, 1192, 1165, 1100, 1073, 996, 954, 886, 863, 775, 678.

$^1$H NMR: δ 6.69 (s, 1H, O=C—NH), 4.21 (q, 1H, (R)$_3$CH, J=6.8), 3.82 (q, 6H, Si—O—CH$_2$—CH$_3$, J=7.0), 3.28 (m, 2H, NH—CH$_2$—CH$_2$—CH$_2$—Si), 1.65 (m, 2H, NH—CH$_2$—CH$_2$—CH$_2$—Si), 1.42 (d, 3H, CH$_3$—CH(R)$_2$, J=6.8), 1.23 (t, 9H, Si—O—CH$_2$—CH$_3$, J=7.0), 0.65 (t, 2H, NH—CH$_2$—CH$_2$—CH$_2$—Si, J=8.1).

GC (3 days after preparation): 96.2% N-(3-triethoxysilylpropyl)-2-hydroxypropanamide, 1.7% 3-aminopropyltriethoxysilane and 2.1% lactic acid ethyl ester.

GC (6 weeks after preparation): 95.8% N-(3-triethoxysilylpropyl)-2-hydroxypropanamide, 1.3% 3-aminopropyltriethoxysilane and 2.9% lactic acid ethyl ester.

Example 1b:
N-(3-Triethoxysilylpropyl)-2-hydroxypropanamide

In a round-bottomed flask, 14.01 g (118.6 mmol) of L-lactic acid ethyl ester, 10.00 g of ethanol and 0.15 g of vinyltriethoxysilane were stirred under a nitrogen atmosphere for 10 minutes at 60° C. Then, 25.00 g (112.9 mmol) of 3-aminopropyltriethoxysilane and 0.20 g of Tytan® TAA (titanium acetylacetonate; from Borica Company Ltd.) were added and the mixture was stirred at reflux for 5 h at 100° C. until reaction progress was no longer established by means of IR spectroscopy. The crude product was after-treated for 30 minutes at 80° C. and approx. 10 mbar. This gave a liquid product with a theoretical OH equivalent weight of 293.4 g/Eq, which was stored under the exclusion of moisture at room temperature.

GC (3 days after preparation): 80.4% N-(3-triethoxysilylpropyl)-2-hydroxypropanamide, 19.6% 3-aminopropyltriethoxysilane and <0.1% lactic acid ethyl ester.

Example 2a:
N-(3-Trimethoxysilylpropyl)-2-hydroxypropanamide

In a round-bottomed flask, 16.21 g (90.4 mmol) of 3-aminopropyltrimethoxysilane, 6.20 g (43.05 mmol) of L-lactide and 0.10 g of vinyltrimethoxysilane were stirred under a nitrogen atmosphere for a few minutes at 60° C. until all of the solid was in solution. The mixture was then left to stand for 48 h under nitrogen at 23° C. According to IR spectroscopy, the reaction had concluded. A liquid product with a theoretical OH equivalent weight of 251.4 g/Eq was obtained.

FT-IR: 3410 sh (O—H), 3349 (N—H amide), 2969, 2940, 2841, 1746 (C=O ester), 1651 (C=O amide), 1532 (C=O amide), 1446, 1412, 1367, 1347, 1311, 1279, 1191, 1080, 1038, 963, 884, 864, 808, 776 sh, 677.

Example 2b:
N-(3-Trimethoxysilylpropyl)-2-hydroxypropanamide

In a round-bottomed flask, 12.34 g (118.6 mmol) of L-lactic acid methyl ester, 10.00 g of methanol and 0.15 g of vinyltrimethoxysilane were stirred under a nitrogen atmosphere for 10 minutes at 60° C. Then, 20.25 g (112.9 mmol) of 3-aminopropyltrimethoxysilane and 0.20 g of Tytan® TAA were added and the mixture was stirred at reflux for 6 h at 90° C. until reaction progress was no longer established by means of IR spectroscopy. The crude product was after-treated for 30 minutes at 60° C. and approx. 30 mbar. This gave a liquid product with a theoretical OH equivalent weight of 251 g/Eq.

Example 3:
N-(3-Triethoxysilylpropyl)-2-hydroxyacetamide

In a round-bottomed flask, 21.29 g (96.2 mmol) of 3-aminopropyltriethoxysilane, 5.47 g (47.1 mmol) of 1,4-dioxane-2,5-dione and 0.10 g of vinyltriethoxysilane were stirred under a nitrogen atmosphere for 2 h at 100° C. until reaction progress was no longer established by means of IR spectroscopy. The crude product was after-treated for 10 minutes at 40° C. and approx. 30 mbar. This gave a liquid product with a theoretical OH equivalent weight of 279.4 g/Eq.

FT-IR: 3418 sh (O—H), 3326 (N—H amide), 2973, 2927, 2885, 2735, 1756 (C=O ester), 1655 (C=O amide), 1536 (C=O amide), 1482, 1443, 1411, 1390, 1366, 1350, 1293, 1192, 1165, 1100, 1072, 953, 880, 849, 772, 680.

Example 4:
N-(3-Trimethoxysilylpropyl)-2-hydroxyacetamide

In a round-bottomed flask, 16.21 g (90.4 mmol) of 3-aminopropyltrimethoxysilane, 5.14 g (44.3 mmol) of 1,4-dioxane-2,5-dione and 0.10 g of vinyltrimethoxysilane were stirred under a nitrogen atmosphere for 2 h at 100° C. until reaction progress was no longer established by means of IR spectroscopy. The crude product was after-treated for 10 minutes at 40° C. and approx. 50 mbar. This gave a liquid product with a theoretical OH equivalent weight of 237.3 g/Eq.

FT-IR: 3414 sh (O—H), 3308 (N—H amide), 2941, 2841, 1757 (C=O ester), 1652 (C=O amide), 1533 (C=O amide), 1444, 1412, 1350, 1281, 1191, 1076, 892, 808, 771, 679.

Example 5: N-(3-Triethoxysilylpropyl)-2-hydroxy-2-methylpropanamide

In a round-bottomed flask, 15.67 g (118.6 mmol) of 2-hydroxyisobutyric acid ethyl ester and 0.15 g of vinyltriethoxysilane were stirred under a nitrogen atmosphere for 10 minutes at 60° C. Then, 25.00 g (112.9 mmol) of 3-aminopropyltriethoxysilane and 0.20 g of Tytan® TAA were added and the mixture was stirred for 6 h at 130° C. until reaction progress was no longer established by means of IR spectroscopy. The crude product was after-treated for 30 minutes at 80° C. and approx. 10 mbar. This gave a liquid product with a theoretical OH equivalent weight of 307.5 g/Eq.

FT-IR: 3414 sh (O—H), 3349 (N—H amide), 2973, 2926, 2881, 2735 sh, 1727 (C=O ester), 1649 (C=O amide), 1605 sh, 1533 (C=O amide), 1465, 1446, 1390, 1359, 1344, 1280, 1240, 1163, 1101, 1077, 993, 953, 842, 777, 679.

Example 6: N-(3-Trimethoxysilylpropyl)-2-hydroxy-2-methylpropanamide

In a round-bottomed flask, 14.00 g (118.6 mmol) of 2-hydroxyisobutyric acid methyl ester and 0.15 g of vinyltrimethoxysilane were stirred under a nitrogen atmosphere for 10 minutes at 60° C. Then, 20.25 g (112.9 mmol) of 3-aminopropyltrimethoxysilane and 0.20 g of Tytan® TAA were added and the mixture was stirred for 5 h at 110° C. until reaction progress was no longer established by means of IR spectroscopy. The crude product was after-treated for 30 minutes at 60° C. and approx. 30 mbar. This gave a liquid product with a theoretical OH equivalent weight of 265.4 g/Eq.

FT-IR: 3410 sh (O—H), 3353 (N—H amide), 2969, 2940, 2840, 1746 (C=O ester), 1650 (C=O amide), 1609 sh, 1531 (C=O amide), 1464, 1411, 1368, 1280, 1188, 1078, 1019, 969, 936, 909, 854, 804, 678.

Example 7: N-(n-Butyl)-N-(3-trimethoxysilylpropyl)-2-hydroxypropanamide

In a round-bottomed flask, 23.55 g (100.1 mmol) of N-(n-butyl)-3-aminopropyltrimethoxysilane, 7.00 g (48.6 mmol) of L-lactide, 0.30 g of Tytan® TAA and 0.10 g of vinyltrimethoxysilane were stirred under a nitrogen atmosphere for 30 h at 120° C. until reaction progress was no longer established by means of IR spectroscopy. The crude product was after-treated for 30 minutes at 60° C. and approx. 10 mbar. This gave a liquid product with a theoretical OH equivalent weight of 307.5 g/Eq.

FT-IR: 3428 (O—H), 2936, 2873, 2840, 1754 (C=O ester), 1708, 1640 (C=O amide), 1535, 1459, 1411, 1371, 1316, 1279, 1190, 1081, 982, 880, 812, 777, 676.

Example 8: N,N-Bis(3-trimethoxysilylpropyl)-2-hydroxypropanamide

In a round-bottomed flask, 34.17 g (100.1 mmol) of N,N-bis(3-trimethoxysilyl-propyl)amine, 7.00 g (48.6 mmol) of L-lactide, 0.30 g of Tytan® TAA and 0.10 g of vinyltrimethoxysilane were stirred under a nitrogen atmosphere for 30 h at 120° C. until reaction progress was no longer established by means of IR spectroscopy. The crude product was after-treated for 30 minutes at 60° C. and approx. 10 mbar. This gave a liquid product with a theoretical OH equivalent weight of 413.6 g/Eq.

FT-IR: 3436 (O—H), 2941, 2840, 1756 (C=O ester), 1709, 1643 (C=O amide), 1533, 1457, 1411, 1371, 1346, 1314, 1283, 1254, 1189, 1076, 984, 880, 808, 777, 677.

2. Use as Adhesion Promoter

Example 9

1.0% by weight of hydroxysilane from example 1a was dissolved in absolute ethanol. This solution was used as activator (adhesion promoter solution) on glass. For this, a glass plate (Floatglas; Rocholl, Schönbrunn, Germany) with the dimensions 10×15 cm was affixed on the air side longitudinally with spacer tape such that three glass strips each measuring 2×13 cm were obtained. Each strip was cleaned with acetone and then wiped once with a hygiene wipe wetted with the prepared activator. After a ventilation time of 2 h in the NK, 7.8 g of a MDI polymer, the preparation of which is described below, was applied per strip in a layer thickness of approx. 3 mm. As reference, a second glass plate was treated identically, but instead of the activator pure ethanol was used. The two glass plates were stored in the NK.

After 4 days in the NK, the MDI polymer had completely cured through. On the reference plate treated only with ethanol, the polymer could be pulled off of the glass substrate with minimal application of force. It did not have good adhesion to the glass. On the plate treated with the activator, the fully cured polymer could not be pulled off of the glass substrate. Even after several cuts crossways to the strip direction down to the glass substrate, with which the polymer was cut away from the glass, and pulling away of the polymer strip in a perpendicular upwards manner, the polymer could not be detached from the glass substrate. The hydroxysilane from example 1a in the activator had decisively improved the adhesion of the MDI polymer on glass.

The MDI polymer used was prepared by reacting, under the exclusion of moisture, 845 g of polyol Acclaim® 4200 N (polypropyleneoxidediol, OH number 28.5 mg KOH/g, from Bayer) and 115 g of 4,4'-methylenediphenyl diisocyanate (MDI; Desmodur® 44 MC L, from Bayer) by a known process at 80° C. to give a polyurethane polymer with a titrimetrically determined content of free isocyanate groups of 1.96% by weight. The product was cooled to room temperature and stored under the exclusion of moisture.

3. Use for the Preparation of Silane-Functional Compounds

Example 10: Preparation of an Isocyanatosilane

In a round-bottomed flask, 8.00 g (27.3 mmol) of hydroxysilane from example 1a, 6.06 g (27.3 mmol) of isophorone diisocyanate (Vestanat® IPDI, from Evonik) and 0.03 g of bismuth tris(neodecanoate) (10% by weight in DIDP) were stirred under a nitrogen atmosphere for 4 h at 80° C. and then stored for 4 days under the exclusion of moisture at room temperature. A high-viscosity product with a titrimetrically determined content of free isocyanate groups of 8.2% by weight was obtained.

FT-IR: 3436 sh, 3312 (N—H amide), 3090, 2973, 2927, 2894, 2254 (N=C=O), 1704 (C=O urethane), 1661 (C=O amide), 1532 (C=O amide), 1462, 1445, 1411, 1388, 1365, 1303, 1237, 1194, 1164, 1102, 1075, 955, 904, 857, 773.

Example 11: Preparation of an Isocyanatosilane

In a round-bottomed flask, 8.00 g (27.3 mmol) of hydroxysilane from example 1a, 4.74 g (27.3 mmol) of 2,4-tolylene diisocyanate (Desmodur® T-100, from Bayer) were stirred under a nitrogen atmosphere for 4 h at 80° C. and then stored for 4 days under the exclusion of moisture at room temperature. This gave a very high-viscosity product with a titrimetrically determined content of free isocyanate groups of 6.5% by weight.

FT-IR: 3427 sh, 3295 (N—H amide), 3099, 2974, 2927, 2885, 2267 (N=C=O), 1732 (C=O urethane), 1658 (C=O amide), 1617, 1596, 1537 (C=O amide), 1445, 1413, 1387, 1367, 1306, 1276, 1221, 1165, 1099, 1074, 995, 953, 874, 767, 703, 677.

Example 12: Preparation of a Silane-Functional Polymer

In a round-bottomed flask, 100.00 g of an IPDI polyurethane polymer with a content of 0.63% by weight of free isocyanate groups, the preparation of which is described below, were stirred with 4.84 g of the hydroxysilane from example 1a under a nitrogen atmosphere for 2 h at 90° C. until isocyanate groups were no longer detectable by means of IR spectroscopy. The polymer was cooled to room temperature and stored under the exclusion of moisture.

The polymer was storage-stable under the exclusion of moisture. If it were admixed with 2.5% by weight of Tyzor® IBAY (bis(ethylacetoacetato)diiso-butoxytitanium(IV), from Dorf Ketal) and poured out over an area in a layer thickness of 2 to 3 mm, then it cured in the standard operating environment within 2 weeks to give an elastic material with a dry surface.

The IPDI polyurethane polymer used was prepared by heating, under the exclusion of moisture, 1000 g of Polyol Acclaim® 12200 (polyoxypropylenediol with a low degree of unsaturation, from Bayer; OH number 11.0 mg KOH/g), 43.6 g of isophorone diisocyanate (Vestanat® IPDI, from Evonik), 126.4 g of diisodecyl phthalate (DIDP) and 0.1 g of bismuth tris(neodecanoate) (10% by weight in DIDP) with constant stirring to 90° C. and leaving the mixture at this temperature until the titrimetrically determined content of free isocyanate groups had reached a stable value of 0.63% by weight. The product was cooled to room temperature and stored under the exclusion of moisture.

Example 13: Preparation of a Moisture-Cure Composition 15.00 parts by weight (GT) of the silane-functional polymer from example 12 were processed with 20.00 GT of diisodecyl phthalate, 2.00 GT of a thixotroping paste, the preparation of which is described below, 1.00 GT of vinyltriethoxysilane, 10.00 GT of precipitated calcium carbonate (Socal® U1 S2 from Solvay), 50.00 GT of ground calcium carbonate (Omyacarb® 5 GU from Omya) and 1.25 GT of bis(ethylacetoacetato)diisobutoxytitanium(IV) (Tyzor® IBAY from Dorf Ketal) in a vacuum mixer at 50° C. under the exclusion of moisture for 30 minutes to give a homogeneous paste and stored. The thixotroping paste was prepared by initially introducing 300 g of diisodecyl phthalate and 48 g of 4,4'-methylenediphenyl diisocyanate (Desmodur® 44 MC L; from Bayer) in a vacuum mixer, gently heating them and then slowly adding 27 g of monobutylamine dropwise with vigorous stirring. The resulting paste was further stirred for one hour in vacuo and with cooling.

To determine the skin formation time, a few grams of the composition were applied to boxboard in a layer thickness of approx. 2 mm and, in the standard operating environment, the time was determined until residues no longer remained for the first time on the pipette when gently tapping the surface of the composition using a pipette made of LDPE.

To determine the mechanical properties, the composition was poured onto a PTFE-coated foil to give a film with a thickness of 2 mm, which was stored for 2 weeks in the standard operating environment, a few dumbbells with a length of 75 mm with a bar length of 30 mm and a bar width of 4 mm were punched from the film and these were tested in accordance with DIN EN 53504 at a tensile velocity of 200 mm/min as to tensile strength (breaking force), elongation at break and modulus of elasticity.

The Shore A hardness was determined in accordance with DIN 53505 on test pieces cured for 2 weeks in the standard operating environment.

The following results were obtained:
Skin formation time: 55 minutes,
Tensile strength: 1.50 MPa,
Elongation at break: 150%,
Modulus of elasticity (at 0.5-50% elongation): 1.19 MPa,
Shore A: 38.

As a measure of the thermal resistance, a few dumbbells, or the Shore A test piece, were stored following the 2 weeks in the standard operating environment for an additional 4 weeks at 100° C. in a forced-air oven and then tested in the same manner as to tensile strength, elongation at break and modulus of elasticity, or Shore A hardness.

Following this high-temperature storage, the following results were obtained:
Tensile strength: 0.94 MPa,
Elongation at break: 125%,
Modulus of elasticity (at 0.5-50% elongation): 0.77 MPa,
Shore A: 28.

The moisture-cure composition from example 13 can be used in particular as elastic adhesive and/or sealant.

The invention claimed is:

1. A process for producing a hydroxysilane of the formula (I),

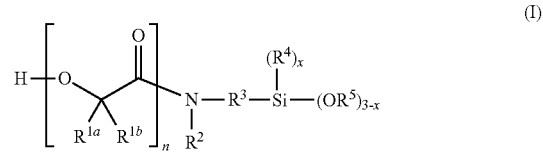

where
$R^{1a}$ and $R^{1b}$, independently of one another, are in each case a hydrogen atom or a monovalent hydrocarbon radical having 1 to 12 carbon atoms, or together are an alkylene radical having 2 to 6 carbon atoms;
$R^2$ is a hydrogen atom or a monovalent hydrocarbon radical having 1 to 12 carbon atoms which optionally comprises ether groups, ester groups, nitrile groups, amino groups or silane groups;
$R^3$ is a linear or branched alkylene or cycloalkylene radical having 1 to 20 carbon atoms, optionally with aromatic fractions, and optionally with one or more heteroatoms;
$R^4$ is an alkyl radical having 1 to 8 carbon atoms;
$R^5$ is an alkyl radical having 1 to 10 carbon atoms which optionally comprises ether groups;
n is 1 or 2; and
x is 0, 1 or 2, the process comprising:
reacting at least one lactide of the formula (II) or at least one hydroxy ester of the formula (III) with at least one aminosilane of the formula (IV),

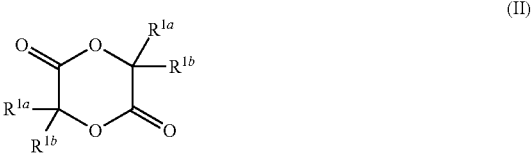

where
m is an integer from 1 to 100; and
$R^6$ is a monovalent hydrocarbon radical having 1 to 12 carbon atoms.

2. The process as claimed in claim 1, wherein it is carried out with at least one lactide of the formula (II).

3. The process as claimed in claim 1, wherein the produced hydroxysilane is at least 95.8% pure.

4. The process as claimed in claim 1, wherein $R^{1a}$ and $R^{1b}$, independently of one another, are in each case a hydrogen atom or a methyl radical.

5. The process as claimed in claim 1, wherein $R^2$ is a hydrogen atom or an alkyl radical or a cycloalkyl radical or an alkoxysilylalkyl radical.

6. The process as claimed in claim 1, wherein $R^3$ is selected from the group consisting of 1,3-propylene, 4-aza-1,6-hexylene, 2-methyl-1,3-propylene, 1,4-butylene, 3-methyl-1,4-butylene and 3,3-dimethyl-1,4-butylene.

7. The process as claimed in claim 1, wherein $R^5$ is a methyl radical or ethyl radical.

8. The process as claimed in claim 1, wherein x is 1 or 0.

9. The process as claimed in claim 1, wherein the hydroxysilane is selected from the group consisting of N-(3-triethoxysilylpropyl)-2-hydroxyacetamide, N-(3-trimethoxysilylpropyl)-2-hydroxyacetamide, N-(3-diethoxymethylsilylpropyl)-2-hydroxyacetamide, N-(3-dimethoxymethylsilylpropyl)-2-hydroxyacetamide, N-(3-triethoxysilylpropyl)-2-hydroxypropanamide, N-(3-trimethoxysilylpropyl)-2-hydroxypropanamide, N-(3-diethoxymethylsilylpropyl)-2-hydroxypropanamide, N-(3-dimethoxymethylsilylpropyl)-2-hydroxypropanamide, N-(3-triethoxysilylpropyl)-2-hydroxy-2-methylpropanamide, N-(3-trimethoxysilylpropyl)-2-hydroxy-2-methylpropanamide, N-(3-diethoxymethylsilylpropyl)-2-hydroxy-2-methylpropanamide and N-(3-dimethoxymethylsilylpropyl)-2-hydroxy-2-methylpropanamide.

10. The process as claimed in claim 1, further comprising reacting the hydroxysilane with at least one compound which has at least one group that is reactive towards hydroxyl groups to form a silane-functional compound.

11. The process as claimed in claim 10, wherein the group that is reactive towards hydroxyl groups is selected from the group consisting of isocyanate groups, epoxy groups, acrylate groups, methacrylate groups, anhydride groups, carboxylic acid groups, ester groups, carbonate groups and cyclocarbonate groups.

12. The process as claimed in claim 10, wherein the compound which has at least one group that is reactive towards hydroxyl groups is selected from the group consisting of isocyanatosilanes, diisocyanates, their oligomers and derivatives, and polymers having isocyanate groups.

13. The process as claimed in claim 1, further comprising forming a curable composition that comprises the hydroxysilane or a silane-functional compound obtained from the reaction of at least one of the hydroxysilane with at least one compound which has at least one group that is reactive towards hydroxyl groups as constituent.

14. The process as claimed in claim 13, further comprising utilizing the curable composition as a pretreatment agent or a coating or a sealant or an adhesive.

15. The process as claimed in claim 13, further comprising forming an article from the curable composition.

* * * * *